(12) United States Patent
Vinton et al.

(10) Patent No.: US 8,722,961 B2
(45) Date of Patent: May 13, 2014

(54) HYPERBARIC DRESSING

(75) Inventors: Melvin Frederick Vinton, Fowlmere (GB); Allan Hurst, Little Ouse (GB); Derek Fray, Great Shelford (GB)

(73) Assignee: Inotec and Limited, Cambridge, Cambridgeshire (GB)

( * ) Notice: Subject to any disclaimer, the term of this patent is extended or adjusted under 35 U.S.C. 154(b) by 1022 days.

(21) Appl. No.: 11/547,412

(22) PCT Filed: Apr. 1, 2005

(86) PCT No.: PCT/GB2005/001299
§ 371 (c)(1),
(2), (4) Date: Dec. 14, 2007

(87) PCT Pub. No.: WO2005/094744
PCT Pub. Date: Oct. 13, 2005

(65) Prior Publication Data
US 2008/0269658 A1 Oct. 30, 2008

(30) Foreign Application Priority Data
Apr. 2, 2004 (GB) .................................. 0407502.4

(51) Int. Cl.
*A61F 13/00* (2006.01)

(52) U.S. Cl.
USPC .................. 602/47; 602/42; 602/43; 602/48; 604/304; 604/305; 424/443; 424/445

(58) Field of Classification Search
USPC .............. 602/42, 43, 47, 48, 54–56; 604/304, 604/305, 307, 308; 424/443, 445
See application file for complete search history.

(56) References Cited

U.S. PATENT DOCUMENTS

| | | | | |
|---|---|---|---|---|
| 3,610,238 A | * | 10/1971 | Rich, Jr. ......................... | 604/23 |
| 4,608,041 A | * | 8/1986 | Nielsen .......................... | 604/23 |
| 4,969,881 A | | 11/1990 | Viesturs ........................ | 604/305 |
| 5,018,515 A | | 5/1991 | Gilman ......................... | 128/155 |
| 5,308,313 A | | 5/1994 | Karami et al. .................. | 602/55 |
| 5,465,735 A | * | 11/1995 | Patel ............................. | 128/888 |
| 6,423,018 B1 | * | 7/2002 | Augustine ........................ | 602/2 |
| 2002/0065494 A1 | * | 5/2002 | Lockwood et al. ........... | 604/313 |
| 2004/0030304 A1 | | 2/2004 | Hunt et al. | |

* cited by examiner

*Primary Examiner* — Patricia Bianco
*Assistant Examiner* — Keri J Nelson
(74) *Attorney, Agent, or Firm* — Nexsen Pruet, LLC (57) ABSTRACT

A hyperbaric dressing has a fluid impermeable sheet and a fluid permeable layer with a sheet of porous material positioned between these two layers with passageways to permit fluid to flow out of the dressing.

16 Claims, 5 Drawing Sheets

HYPERBARIC DRESSING

This invention relates to a hyperbaric dressing for use in the treatment of wounds, more particularly, a hyperbaric dressing for supplying oxygen to a wound and for allowing or causing exudate to be removed from the wound.

It is known that a supply of oxygen to a wound or through the skin covering a wound promotes healing and reduces scarring of damaged tissue. Typically, oxygen is absorbed by tissue fluids, thus improving the oxygen content of intercellular fluids and/or promoting metabolism and repair of the damaged tissue. As such, there are numerous ailments which may benefit from the topical application of oxygen to damaged tissue, for example, osteomylelitis, tendon, ligament and cartilage damage, fractures, burns, scalds, necrotising fasciitis, such as pyoderma gangrenosum, pressure-induced decubitus (bed sores), venous and diabetic foot and leg ulcers, as well as cuts, abrasions and surgically induced wounds and incisions.

At present, there are several methods for supplying a wound with oxygen. One such method is to place the entire affected limb within a sealed container which controls oxygen pressure within the container. However, these containers are expensive, difficult to sterilise and may limit a patient's mobility. Furthermore, as a whole limb is placed within the container, large areas of normal tissue are subjected to high concentrations of oxygen. Thus, there is a need for a remedy for locally supplying a wound with oxygen without the associated disadvantages of prior art methods discussed above.

Accordingly, one aspect of the invention resides in a hyperbaric dressing comprising first and second layers and delivery means arranged to supply a fluid, such as a gas, to the first layer, wherein the first layer is associated with the second layer to allow the fluid to flow in one direction through the second layer and to allow another fluid, such as a liquid, to flow in the opposite direction through the second and first layers.

The hyperbaric dressing may further comprise a self-adhesive layer, preferably adjacent the second layer, with a peel-off backing layer to enable the dressing to be affixed to a surface, such as a patient's skin surrounding a wound. The adhesive of any such self-adhesive layer may extend over the whole area of that layer or partially thereover. In the latter case, the adhesive may be in strip form extending around the second layer between the peripheral edges of the first and second layers.

When the first fluid is a gas, the other fluid may be a liquid or vice-versa.

The first and/or second layer may be a gas-permeable layer.

The first and second layers may be secured together by means of sonic welding or induction heating, for example. Typically, this involves sealing the peripheral edges of the layers together to form, say, a pouch and, possibly, sealing together in-register portions of the first and second layers. Any gas-impermeable first layer may be formed, for example by vacuum, into recesses such as circular recesses, whose bases may be secured to in-register portions of the second layer, with passageways extending through the remainder of the first layer between any such recesses for the transmission of, say, oxygen or other fluid through the passageways.

The first and second layers are typically made of suitable plastics materials and, preferably, the first layer is made of polyurethane.

The layers are typically in the range of 0.05 mm to 1 mm thick and most preferably in the range of 0.1 mm to 0.5 mm thick.

Additionally, where adjacent portions of the two layers are sealed together, or otherwise associated with each other, holes or other perforations through both layers and, optionally, any self-adhesive layer can be made. These holes can be made by any appropriate method, such as, laser drilling. The diameters of the holes should be such that liquids, such as exudate from a wound, may pass through them, and, hence, through the second and first layers, with comparative ease.

Alternatively, the first layer may comprise a sheet of porous material, such as an open cell foam material, which is permeable to a fluid, such as a gas, and which is adjacent the second layer, with a fluid impermeable sheet applied to the outer surface of the porous sheet remote from the second layer.

The porous sheet is preferably provided with means for communication with a source of gas, for example, an oxygen generator.

In a preferred embodiment to be described in more detail hereinbelow, the porous sheet is provided with an array of apertures through which the fluid impermeable outer sheet and second layer can be sealed together, with further holes provided therein for allowing or causing a fluid, such as exudate from a wound to which the dressing is applied, to flow through the second and first layers in a direction opposite to that of the flow of gas, such as air or oxygen, through the second layer and on to the associated wound.

The further holes may be formed by any suitable means during manufacture of the dressing, for example, by laser drilling through the sealed-together fluid impermeable sheet of the first layer and the second layer.

In this manner, and when the dressing is in use and applied to a wound, oxygen can be caused to flow through the porous sheet of the first layer and through the gas permeable second layer to the wound, whilst any exudate from the wound can flow in the reverse direction to the oxygen through the second and first layers via the further holes, as discussed above.

The fluid-delivery means may be arranged to supply to the dressing any suitable gas, for example air, although the most preferred gas is oxygen.

Typically, the fluid-delivery means is a tube. One end of the tube may be attached, either releasably or permanently, for example sealed, to the dressing, with the other end being capable of being connected, via appropriate means, to a gas cylinder, compressor or other supply of gas. Preferably, that other tube end is attachable to are oxygen cylinder or gas generator which is preferably portable.

In an embodiment to be described hereinbelow, the fluid-delivery means, which is essentially a gas-delivery means, is integral with the two layers of the dressing, with portions thereof forming a tube for attachment to, say, an oxygen source. In this case, two spaced sealing lines can form the integral tube between the two layer portions of the dressing.

It will, of course, be appreciated that many different sizes of dressing could be required, depending upon the size of the wounds to be dressed. Thus, dressings may be formed into any appropriate shape and be of any suitable size. Alternatively, the dressings may be cut to size.

Furthermore, more than one gas-delivery device may be utilised to help standardise the amount of oxygen passing through the dressing throughout the whole wound-covering area of the dressing.

In use, this dressing can be applied to a wound by way of removing any peel-off layer to expose any self-adhesive layer and then placing the dressing directly over the wound, the exposed self-adhesive layer(s) preferably being placed upon unaffected skin around the wound.

A standard absorbent or compression bandage can then be placed over the dressing to soak up any exudate which seeps from the wound. Oxygen is supplied to the dressing via the gas-delivery means and, in turn, pressurises the dressing forcing the oxygen into contact with the wound.

Additionally or alternatively, exudate may be removed by other suitable means, for example, a vacuum source connected to the exterior of the dressing.

A second aspect of the invention resides in a hyperbaric dressing comprising first and second layers and delivery means arranged to supply a fluid, such as a gas, to between the two layers, wherein the delivery means is integral with the first and second layers, preferably being formed as a tube from portions of those two layers.

The invention also provides, in combination, a hyperbaric dressing as defined above in accordance with the first or second aspect thereof or any modification described above and an absorbent or compression outer bandage or dressing. Each outer bandage or dressing may substantially seal any un-sealed or cut edges of a hyperbaric dressing, so as to allow hyperbaric fluid pressure to be maintained.

Further, the invention can provide, in combination, a hyperbaric dressing as defined above in accordance with the first or second aspect of the invention, or any modification thereof, and a portable oxygen generator connected or connectable to the fluid delivery means.

In a third aspect, the invention provides a method of cosmetically treating a human being or animal to reduce the existence and/or visibility of scar tissue following surgery or illness, comprising the steps of:

placing a hyperbaric dressing, in accordance with the first or second aspect of the invention defined above or any modification thereof, on to a wound; and supplying the so-applied dressing, and thus the wound, with oxygen, preferably from a portable oxygen generator.

Additional to the above-mentioned method may be the step of applying a standard absorbent or compression bandage over the dressing so as to absorb or otherwise collect any exudate which may seep from the wound through the dressing. Additionally or alternatively, exudate may be removed from the dressing under vacuum.

In order that the present invention may be more fully understood, embodiments of hyperbaric dressings will now be described by way of example and with reference to the accompanying drawings in which.

Figure 2:
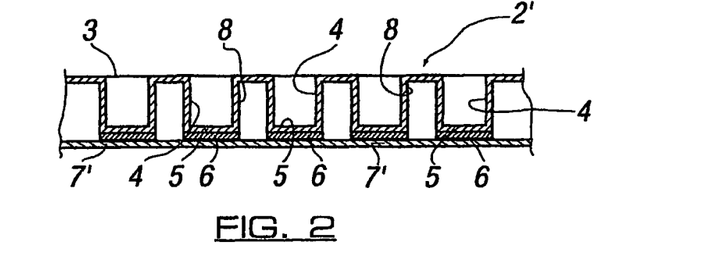
FIG. 2 is a section, in elevation, of the first upper layer of the hyperbaric dressing, as shown in FIG. 1, secured to a second lower layer of the partially-formed dressing.
Figure 3:
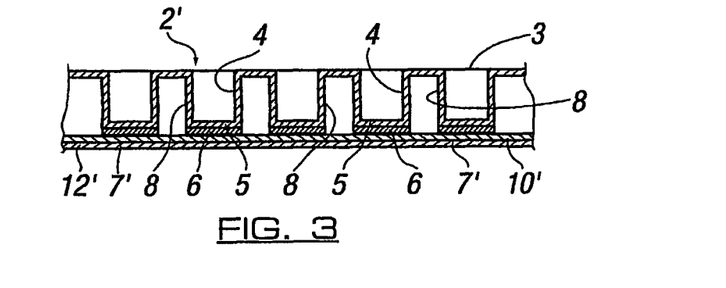
FIG. 3 is a section, again in elevation, of the upper and lower layers of the partially-formed dressing, as shown in FIG. 2, with a self-adhesive layer attached removably to the lower layer.
Figure 4:
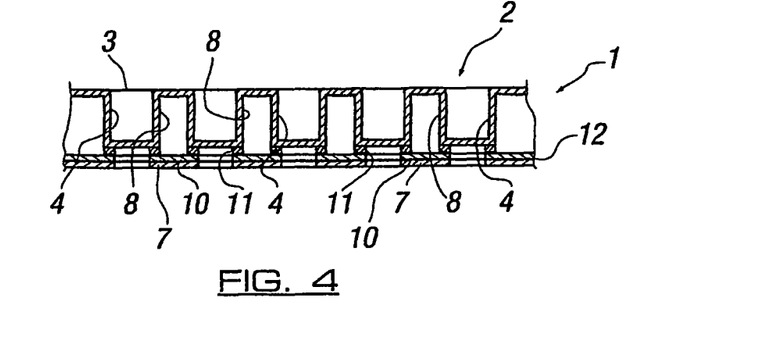
FIG. 4 is a section, again in elevation, of the hyperbaric dressing in its final form.
Figure 5:
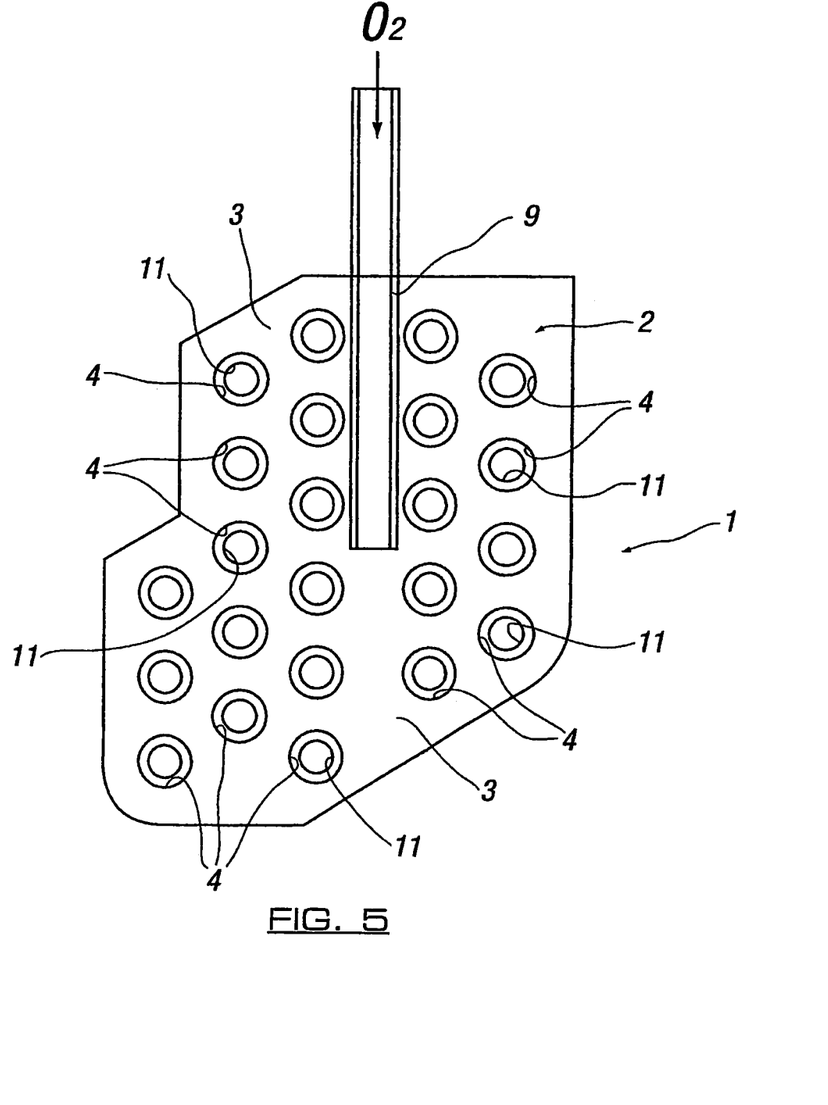
FIG. 5 is a plan view of the dressing shown in FIG. 4.

Referring firstly to FIGS. 1 to 5 of the accompanying drawings, a first embodiment of hyperbaric dressing, indicated generally at 1 in FIGS. 4 and 5, comprises a first, upper layer 2 which is formed as follows.

Figure 1:
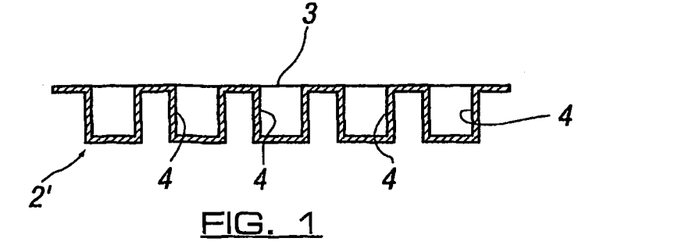
FIG. 1 is a section, in elevation, of a first upper layer of a first embodiment of hyperbaric dressing.

A partially-formed first, upper layer, indicated generally at 2' in FIGS. 1 to 3, comprises a flexible, polyurethane film 3 which is 0.01 mm to 0.05 mm thick, is hydrophilic and is gas, namely oxygen, impermeable. The film 3 has circular recesses 4 vacuum formed therein, with the bases 5 of the recesses 4 bonded at 6 to a partially-formed second, lower layer 7' which is gas, namely oxygen, permeable and hydrophobic. In this manner, passageways 8 for the transmission of oxygen therethrough, are provided between the gas impermeable, hydrophilic first, upper layer 2' and gas permeable, hydrophobic second, lower layer 7', such passageways being in communication with a tube 9 connected to a source of oxygen (not shown).

As shown in FIG. 3, a partially-formed, peel-off layer 10' and self-adhesive layer 12' are provided on the underside of the lower layer 7'.

Figure 6:
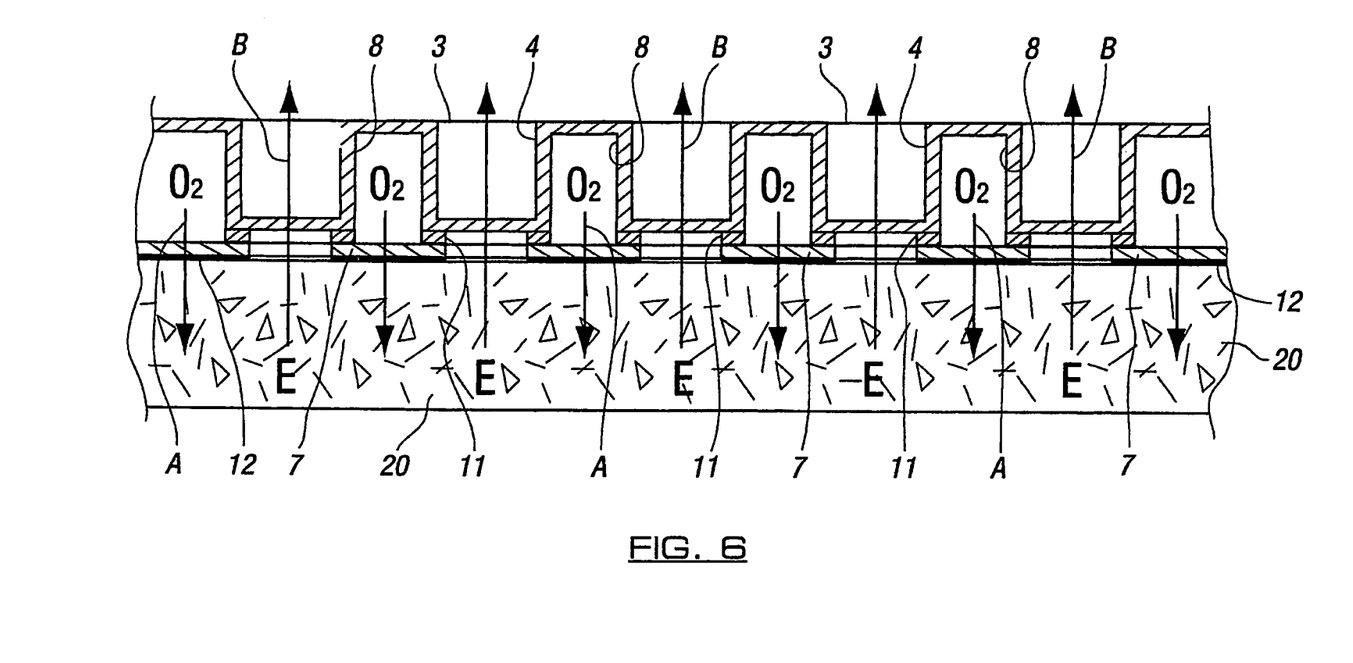
FIG. 6 is a sectional diagrammatic view of the dressing shown in FIGS. 4 and 5 in use.

To form the final hyperbaric dressing, as shown generally at 1 in FIGS. 4 to 6, holes 11 are punched, or otherwise formed, through the bases 5 of the circular recesses 4, the lower layer 7' and the peel-off and self-adhesive layer 10', 11'. Thus, the final dressing 1, as shown in FIGS. 4 to 6, comprises perforated first, upper, second, lower and self-adhesive, peel-off layers 2, 7, 10, 12.

The so-formed dressing 1 is pouch-like in nature, with the peripheries of the layers 2, 7 sealed together.

FIG. 6 shows the hyperbaric dressing 1 in use, wherein the peel-off layer 10 has been removed from the self-adhesive layer 11 and the dressing 1 has been positioned on a patient's skin covering a wound 20.

Oxygen at a pressure greater than atmospheric pressure is fed from a portable oxygen generator (not shown) through the tube 9 into the passageways 8 of the dressing 1 which, as a compresse, becomes partially inflated. The oxygen pressure inside the dressing 1 forces some oxygen through the second, lower gas-permeable layer 7, as indicated by $O_2$ and the one direction arrows A in FIG. 6, and on to the wound 21. Any exudate from the wound 20, as indicated by E, in FIG. 6, migrates from the wound 20 through the holes 11 in the other direction of arrows B to the side of the dressing 1 remote from the wound 20. At this point the exudate E can be absorbed by an outer absorbent bandage (not shown) or removed under vacuum.

Rather than using a portable oxygen generator, oxygen may be provided at the necessary pressure against atmospheric pressure by any other suitable means, for example, an oxygen cylinder or oxygen generator, connected to the remote end of the tube 9.

Figure 7:
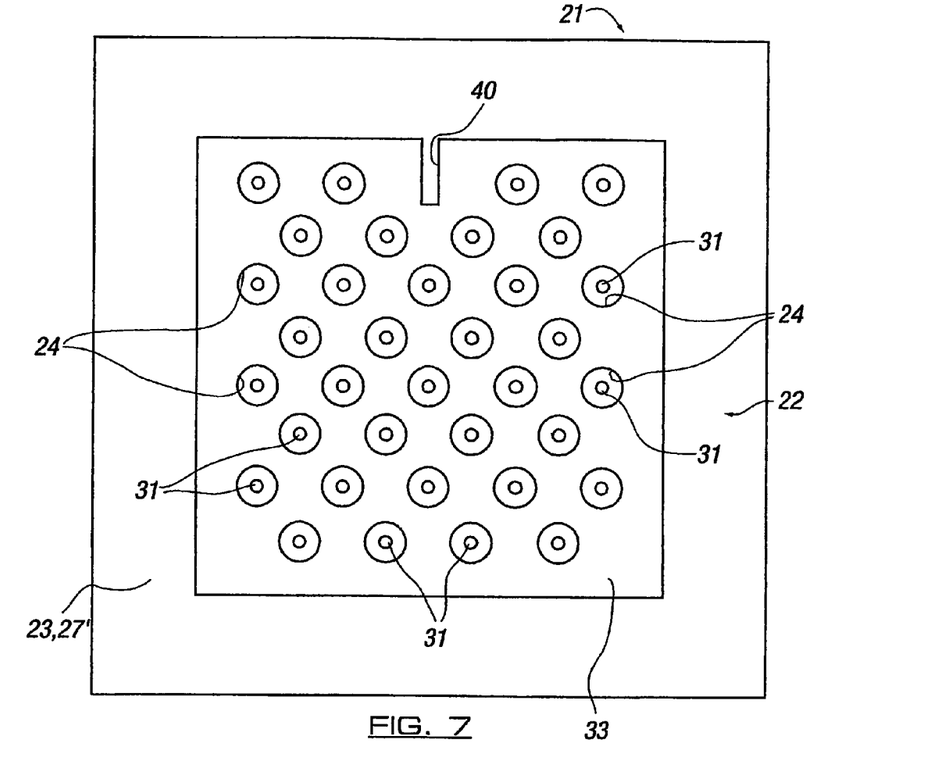
FIG. 7 is a plan view of a second embodiment of hyperbaric dressing.
Figure 8:
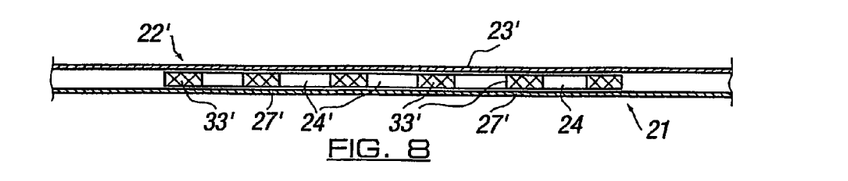
FIG. 8 is a section, in elevation, of the dressing shown in FIG. 7 but in a partially assembled condition prior to full manufacture.
Figure 9:
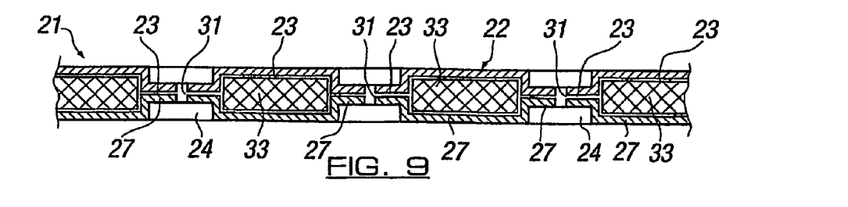
FIG. 9 is a section, again in elevation, of the dressing shown in FIG. 7.

Referring now to FIGS. 7 to 9 of the drawings, a second embodiment of hyperbaric dressing, indicated generally at 21 in FIGS. 7 and 9, comprises a first, upper layer 22 including a gas impermeable sheet 23 of polyethylene film and a thicker sheet 33 of an open cell foam material which is at least gas-permeable and which has a substantially regular array of circular apertures 24 extending through the thickness thereof.

In FIG. 8, there is shown a partially-formed first, upper layer $22^1$ comprising the sheet $23^1$ of gas-impermeable, polyethylene film and the intermediate sheet $33^1$ of open cell foam material, with the circular apertures shown at $24^1$. A second, lower layer $27^1$ is provided by a gas-permeable sheet of a material sold under the Trade Mark "CAPLA".

To form the final hyperbaric dressing, as shown generally at 21 in FIGS. 7 and 9, the outer sheet 23$^1$ of the first layer 22$^1$ and the second, lower layer 27$^1$ are, using a suitable tool (not shown), heat sealed together through the circular apertures 24$^1$. Simultaneously or subsequent to such heat sealing, circular holes 31 are formed through the resulting heat sealed-together sheet 23 of the first layer 22 and the second, lower layer 27 within the apertures 24, as shown in particular in FIG. 9.

As in the case of the first embodiment of hyperbaric dressing 1 discussed above with reference to FIGS. 4 to 6, peel-off and self-adhesive layers (also not shown) may be employed.

In use of the hyperbaric dressing 21, it is applied over a wound and oxygen at a pressure greater than atmospheric pressure is fed from, say, a portable oxygen generator (not shown) through a tube received in a cut-out socket 40 provided in one edge of the open cell foam sheet 33 of the first layer 22. Because the gas impermeable sheet 23 is sealed to the open cell foam sheet 33 of the first layer 22, the oxygen pressure inside the open cell foam sheet 33 forces oxygen through the second, lower gas-permeable layer 27 in one direction and on to the wound.

Because also the second, lower gas-permeable layer 7 is impermeable to liquid, any exudate from the wound migrates therefrom through the holes 31 in the circular apertures 24 in the other direction toward the side of the dressing 21 remote from the wound. At this point, the exudate can be absorbed by an outer absorbent bandage (not shown) or removed under vacuum or by any other suitable means.

As in the case of the first embodiment of hyperbaric dressing 1 described above, rather than using a portable oxygen generator, oxygen may be provided at the necessary pressure against atmospheric pressure by any other suitable means, for example, from an oxygen cylinder connected to the tube inserted in the socket 40.

Figure 10:
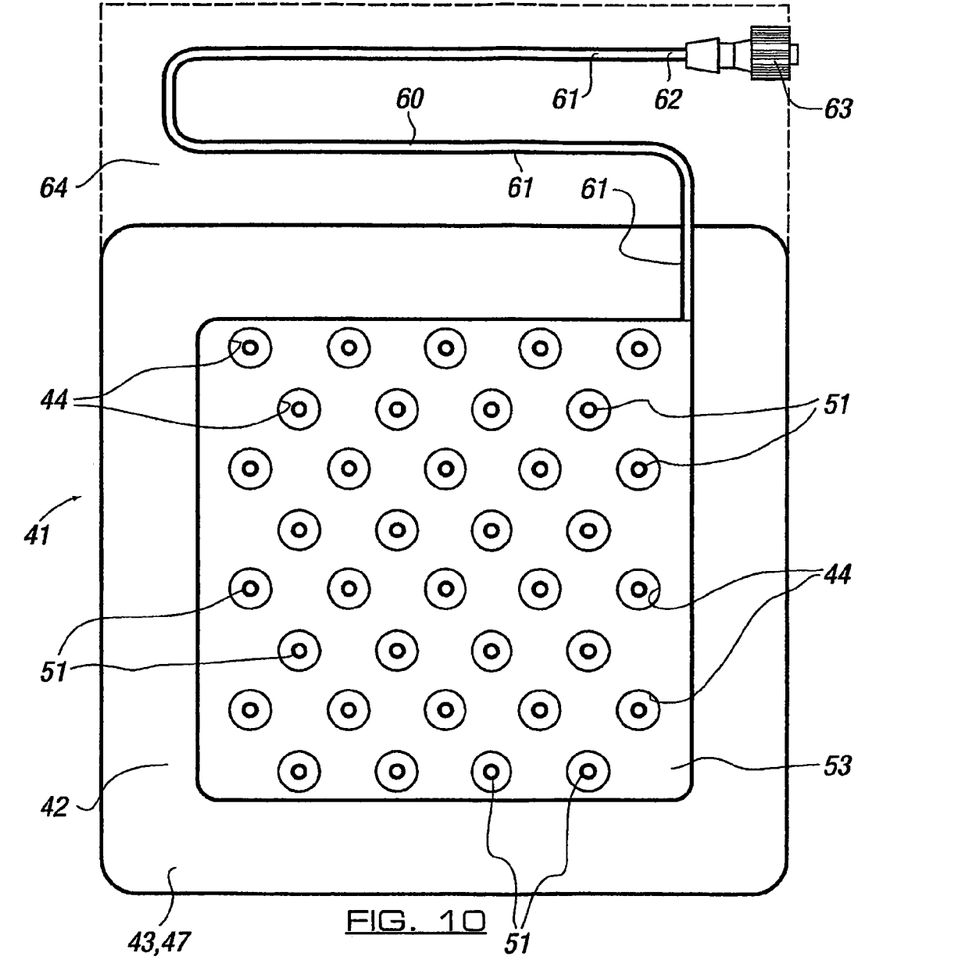
FIG. 10 is a plan view of a third embodiment of hyperbaric dressing.
Figure 11:
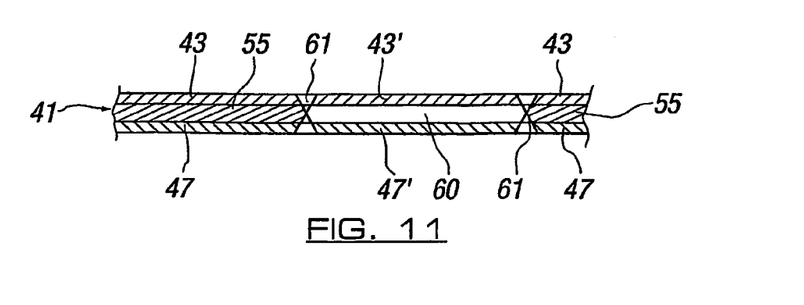
FIG. 11 is a partial sectional view of the dressing shown in FIG. 10.

Turning now to a third embodiment of hyperbaric dressing, as indicated generally at 41 in FIGS. 10 and 11, a first upper layer 42 comprises a gas impermeable sheet 43 of polyethylene film and a thicker sheet 53 of an open cell foam material which is gas-permeable and which has a substantially regular array of circular apertures 44 extending through the thickness thereof.

A second, lower layer 47 is provided by a gas-permeable sheet of material sold under the Trade Mark "CAPLA".

This arrangement is very similar to the second embodiment described above with reference to FIGS. 7 to 9, as are the circular holes 51 extending through both the upper and lower layers 42,47 within the bounds of the apertures 44 of the foam sheet 53.

However, in this third embodiment of dressing, the gas delivery arrangement is provided by an integral tube 60 formed from adjacent portions of the sheet 43 of the first, upper layer 42 and the lower layer 47, as shown in detail in FIG. 11.

Formation of the integral tube 60 is carried out by providing a pair of spaced, sealing weld lines, as shown at 61, between the gas-impermeable sheet 43 of the upper layer 42 and the gas-permeable lower layer 47, the sheet 43 and the layer 47 already having been sealed together at 55 over the major portions of their confronting surfaces. The integral tube 60 is thus formed between respective portions 43$^1$ and 47$^1$ of the sheet 43 and layer 47 which are not sealed together. In use, the end 62 of the tube 60 remote from the dressing 41 can be connected to an oxygen source (not shown) by means of a connector 63.

The spaced sealing weld lines 61 can be formed within the material 64 before it is cut-away or otherwise removed from the dressing 41 during manufacture thereof, such material 64 being constituted by the sheet 43 of the upper layer 42 and the lower layer 47.

It has been found that this integral tube 60 provides a very useful means for supplying oxygen to the interior of the dressing 42 and, also, that only about 2% of oxygen from the oxygen source is lost through that part of the tube 60 constituted by the portion 47$^1$ of the lower layer 47.

Thus, the invention provides a hyperbaric dressing which accomplishes the same function as the known oxygen chambers, bags and the like discussed above but at much less expense. Also, it is more easily positioned upon a patient and is easily removable after use. Further, it is readily disposable and requires no sterilisation after use. During use, a patient can enjoy substantially full mobility, particularly if a small portable oxygen generator or cylinder is available, whilst employing any suitable existing type of absorbent dressing over the hyperbaric dressing for absorbing exudate E through the holes.

The invention claimed is:

1. A hyperbaric dressing comprising;
a first layer and a second layer associated together to form
a) an oxygen supply portion comprising a pouch in which the first layer is a sheet formed of a fluid-impermeable material and the second layer is a sheet formed of a gas-permeable and liquid-impermeable material; and
b) an exudate removal portion comprising at least one sealed-together in-register portion of the first and second layers, defining a hole through the first and second layers; and
a delivery means arranged to supply oxygen to between the first and second layers to pressurize the pouch;
wherein the oxygen can permeate out of the pouch through the second layer, wherein a fluid comprising wound exudate cannot permeate through the second layer into the pouch, and wherein the hole defined through the first and second layers of the at least one sealed-together in-register portion is of such a diameter to allow the fluid comprising wound exudate to flow through the second and first layers.

2. A dressing according to claim 1, further comprising a self-adhesive layer.

3. A dressing according to claim 2, wherein the self-adhesive layer is adjacent the second layer.

4. A dressing according to claim 1, wherein the fluid-impermeable sheet of the pouch is gas-impermeable.

5. A dressing according to claim 1, wherein the peripheral edges of the first and second layers are secured together to form the pouch.

6. A dressing according to claim 1, wherein the first layer includes recesses, wherein bases of the recesses are secured to in-register portions of the second layer.

7. A dressing according to claim 1, wherein the fluid-impermeable sheet and the gas-permeable and liquid-impermeable sheet are made of a plastics material.

8. A dressing according to claim 7, wherein the fluid-impermeable sheet is made of polyurethane.

9. A dressing according to claim 1, wherein the fluid-impermeable sheet and the gas-permeable and liquid-impermeable sheet are in the range of 0.05 mm to 1.00 mm thick or are in the range of 0.1 mm to 0.5 mm thick.

10. A dressing according to claim 1, wherein said delivery means comprises an integrally-formed tube.

11. A dressing according to claim 10, wherein the integrally-formed tube is formed from portions of the first layer and the second layer, by a pair of spaced, sealing lines welding the portions of the first layer and the second layer together, with a space therebetween.

12. In combination, a hyperbaric dressing according to claim 1 and an absorbent or compression outer bandage or dressing for absorbing exudate or vacuum means for the removal of exudate.

13. A dressing according to claim 1, in which the pouch comprises a sheet of porous material positioned between the fluid-impermeable sheet and the gas-permeable and liquid-impermeable sheet.

14. A dressing according to claim 13, wherein the sheet of porous material is adjacent the gas-permeable and liquid impermeable sheet.

15. A dressing according to claim 14, wherein the fluid impermeable sheet is applied to the outer surface of the porous sheet remote from the gas-imermeable and liquid-impermeable sheet.

16. A dressing according to claim 14, wherein an array of apertures is defined in the porous sheet, through which apertures the first layer and the second layer are sealed together to form the at least one sealed-together in-register portion of the first and second layers.

\* \* \* \* \*

UNITED STATES PATENT AND TRADEMARK OFFICE
CERTIFICATE OF CORRECTION

| | |
|---|---|
| PATENT NO. | : 8,722,961 B2 |
| APPLICATION NO. | : 11/547412 |
| DATED | : May 13, 2014 |
| INVENTOR(S) | : Melvin Frederick Vinton, Allan Hurst and Derek Fray |

It is certified that error appears in the above-identified patent and that said Letters Patent is hereby corrected as shown below:

On the Title Page

Item (73) Assignee name should read as follows: Inotec AMD Limited.

Signed and Sealed this
Fifth Day of August, 2014

Michelle K. Lee
*Deputy Director of the United States Patent and Trademark Office*